United States Patent [19]

Norton

[11] 4,380,236
[45] Apr. 19, 1983

[54] FLUID PUMP

[75] Inventor: William W. Norton, Lincolnshire, Ill.

[73] Assignee: Baxter Travenol Laboratories, Inc., Deerfield, Ill.

[21] Appl. No.: 301,677

[22] Filed: Sep. 14, 1981

[51] Int. Cl.³ .................................... A61M 5/00
[52] U.S. Cl. ..................... 604/151; 128/DIG. 12; 417/43; 417/44; 604/32; 604/250
[58] Field of Search ............... 417/43, 474, 476, 477, 417/412, 413; 128/214 E, 214 F, DIG. 12, DIG. 13

[56] References Cited

U.S. PATENT DOCUMENTS

| Re. 28,122 | 1/1969 | Dahlstrom . | |
|---|---|---|---|
| 2,208,831 | 7/1940 | Bassett, Jr. . | |
| 2,706,914 | 4/1955 | Spence . | |
| 3,151,616 | 10/1964 | Selfon . | |
| 3,327,898 | 6/1967 | Farr . | |
| 3,798,982 | 3/1974 | Lundquist | 128/214 F |
| 4,184,815 | 1/1980 | Casson et al. | 128/214 F |
| 4,187,057 | 2/1980 | Xanthopoulos | 128/214 F |
| 4,189,286 | 2/1980 | Murray et al. | 417/477 |
| 4,210,138 | 7/1980 | Jess et al. | 128/214 F |
| 4,256,437 | 3/1981 | Brown | 128/214 F |
| 4,278,085 | 7/1981 | Shim | 128/214 F |

Primary Examiner—Richard J. Apley
Assistant Examiner—George Yanulis
Attorney, Agent, or Firm—Paul C. Flattery; Garrettson Ellis; Bradford R. L. Price

[57] ABSTRACT

Apparatus for the administration of solution to a patient at a precisely controlled rate. A length of flexible, collapsible tubing filled with the solution and connectable at one end to a conduit communicating with the vascular system of a patient is advanced through roller means, so that the solution expelled from the tubing is proportional to the rate of advancement of the tubing through the roller means.

34 Claims, 4 Drawing Figures

FLUID PUMP

TECHNICAL FIELD

Many systems for the infusion of medicaments and the like to a patient are known to the prior art, and some of them are currently commercially available. While some of these systems are small enough to be self-contained and worn by the user, a technical problem still exists in providing an apparatus for the essentially continuous administration of a medicament in ultra low dosage.

For example, it would be desirable to have wearable apparatus for the parental administration of insulin on a continuous ultra low dosage basis throughout the day. It may be desired to uniformly and continuously administer insulin to a patient throughout the day at a rate for example of only 0.05 to 1 ml. per 24 hours. Such a dosage, when administered uniformly and substantially continuously throughout the day, comes closest to simulating the natural function of the pancreas in its production of insulin for the body. Other hormones, chemotherapy agents, and the like may also be desired to be administered on a continuous basis in ultra low dosages on the order of 1 cc. per 24 hours. However, at this time no system is known which can effectively provide uniform, continuous administation of an ultra low dosage of no more than about 5 cc. per 24 hours period, broken down so that a tiny fraction of that small amount of material is administered to the patient in essentially every minute of the day.

DESCRIPTION OF PRIOR ART

Selfon U.S. Pat. No. 3,151,616 discloses an automatic transfusion apparatus in which a pair of rollers gradually compress a bag of solution to expel the contents in a predetermined flow rate to the patient.

Farr Pat. No. 3,327,998 teaches a titration means in which capillary tubing passes through a pair of rollers to administer a liquid chemical reagent, and a length of capillary tubing passing the driver and driven rollers is measured as a function of the liquid administered.

Dahlstrom Reissue Pat. No. 28,122, Spence U.S. Pat. No. 2,706,914, and Bassett, Jr. U.S. Pat. No. 2,208,831 disclose various drive mechanisms, transmissions and speed reducing mechanisms for various apparatus unconnected with the uniform, continuous administration of ultra low quantities of liquid.

DESCRIPTION OF INVENTION

By this invention, it becomes possible to administer extraordinarily low quantitites of medicament or the like to a patient, i.e., a substantially uniform flow of liquid amounting to only 0.05 to 1 ml. per 24 hour period, although higher flow rates of liquids may be administered if desired, typically up to about 10 ml. per 24 hour period, although there is no pratical upper limit to the amount administered in accordance with this invention.

The invention of this application is preferably used for the administration of a medicament-containing solutions intravenously or subcutaneously to patients, or for enteral adminstration, but it can be used in other fields as well, for example the administration of critical ingredients in chemical, biochemical, or analytical processes, and the like.

In accordance with this invention, the apparatus comprises a length of flexible, collapsible tubing filled with the solution for administration and connectable at one end to a conduit which typically communicates with the vascular system of a patient. Roller means are provided for gripping and squeezing the tubing, while means for rotating the roller means are provided to advance the tubing through the roller means to expel the solution through the one end of the tubing at a rate which is proportional to the rate of advancement of the tubing through the roller means.

The means for rotating the roller means may comprise a shaft carrying a roller of the roller means, having an arm extending normally of the shaft and carried by it to rotate the shaft and roller means as the arm is moved in one direction. Clutch means are provided to prevent back rotation of the shaft as the arm is moved in a direction opposite to the one direction.

A motor is provided, and cam means rotatable by the motor is positioned to engage the arm, to movingly reciprocate the arm back and forth respecitively in the one and opposite directions. Spring means may be provided to bias the arm against the cam means, so that as the arm reciprocates, the shaft and rollers rotate by a predetermined amount with each reciprocation of the arm means.

It is preferred for the cam means to define an outer bearing surface for engaging the arm, which outer bearing surface defines, in transverse cross section, a uniformly outwardly extending spiral surface extending essentially 360° about the cam means and an essentially radial step surface extending between the beginning and end of the spiral surface. Thus, the cam is rotated in the direction so that the arm is pressed in its one direction by moving outwardly along the uniformly outwardly extending spiral surface. This motion step continues about essentially the full 360° of rotation of the cam means. The rollers are correspondingly moved as the arm moves.

Following this, the arm moves in its direction opposite the one direction essentially instantaneously as it encounters the radial step surface, falling down to the bottom of the spiral, whereby continuous, if slow, rotation of the cam means provides essentially continuous rotation of the roller means. Only a moment exists between the expansion of the arm outwardly along the cam to its outwardmost extreme and the arrival of the arm back to its radially inwardmost portion on the cam, at which point it immediately begins moving outwardly again. As stated, the clutch means prevents any backward rotation of the rollers as the arm moves back in its opposite direction, taking only typically a fraction of a second to move in its opposite direction back to the radially inwardmost point of the cam means.

Typically the roller means comprises a pair of rotationally interengaged rollers between which the tubing extends for squeezing.

The tubing may be stored in a housing, and positioned to pass through the roller means and then to be placed back into the housing. Typically the tubing is coiled inside of a first cylindrical chamber of such a housing, the tubing being placed back into a second cylindrical chamber of the housing after passing through the roller means. The first and second cylindrical chambers may be separated by a disc-shaped wall. The disc-shaped wall may define a central aperture with the tubing extending through the aperture from the first chamber, typically through the second chamber, to the roller means. The second cylindrical member defines a first peripheral aperture to receive tubing from the roller means.

The first chamber also may define a second peripheral aperture, with the one end of the tubing adapted for connection to a conduit extending therethrough for connection with the conduit.

Alternatively, the means for rotating the roller means may comprise a rack and gear system which cooperates with a clutch to permit only rotation of the roller means in one direction as the rack reciprocates back and forth, rotating the gear which in turn impels rotation of the rollers in one direction. A solenoid, for example, can drive the rack with conventional timer means controlling the solenoid so that it operates at a predetermined frequency of operation to intermittently rotate the roller means, to cause advancement of the tubing in intermittent stages separated by pauses of typically 5 to 15 seconds duration, for example.

DESCRIPTION OF SPECIFIC EMBODIMENT

Figure 1:
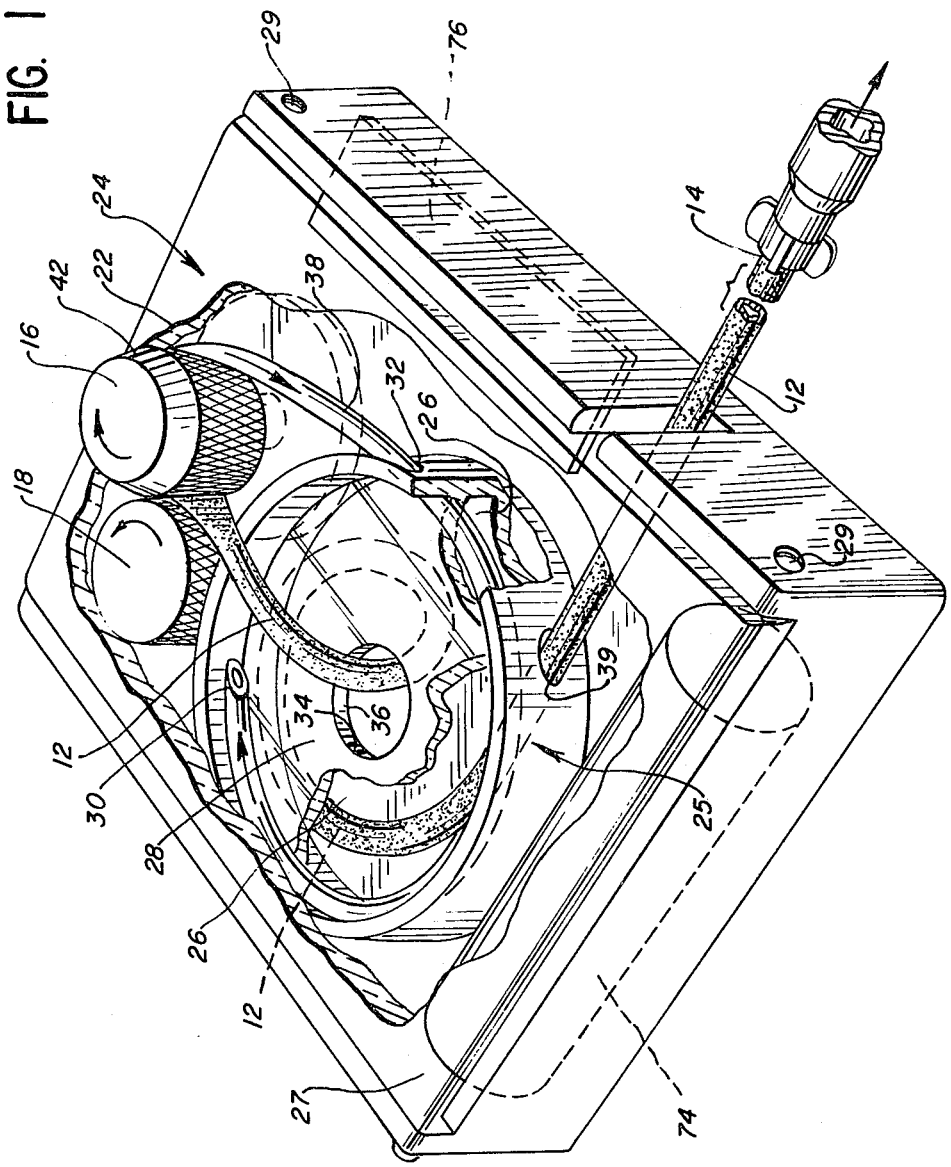
FIG. 1 is a perspective view of an apparatus for administration of solution in accordance with this invention, with portions broken away.
Figure 2:
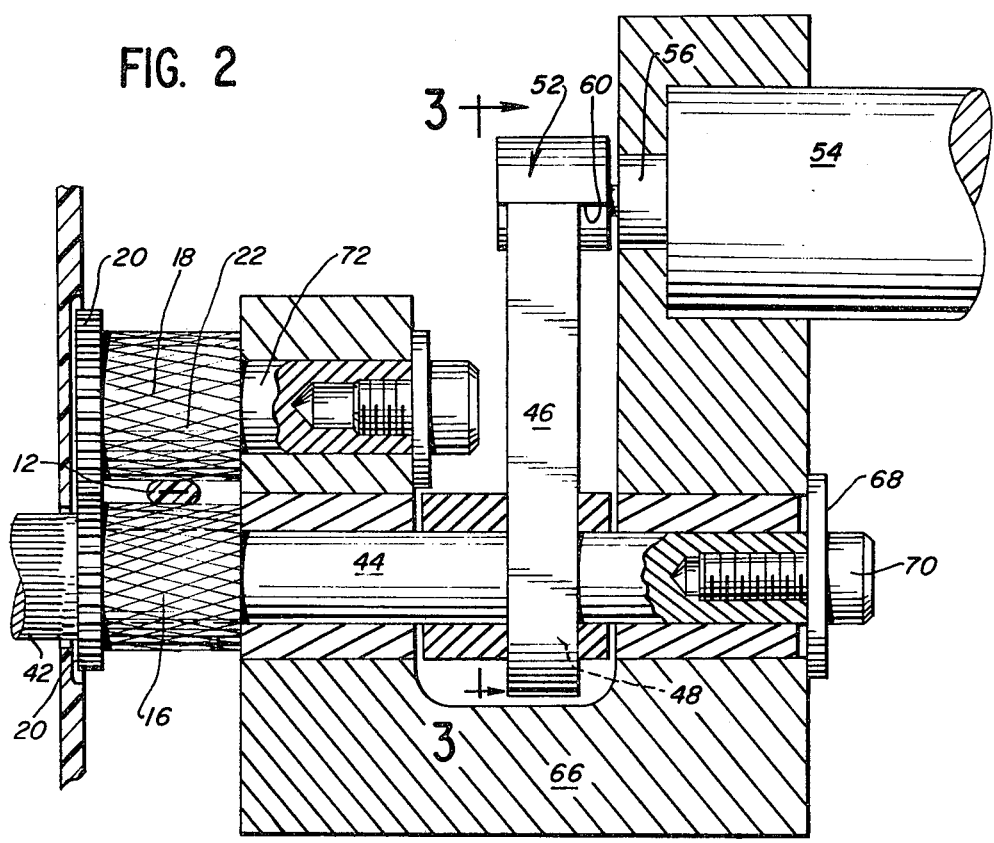
FIG. 2 is a fragmentary view taken partly in section of the means for rotating the rollers utilizable in the apparatus of FIG. 1.

Referring to the drawings, the apparatus for the administration of solution of this invention includes a length of flexible, collapsible tubing 12 having one end 14 which is conventionally adapted for connection with a solution administration set, an IV catheter, a needle, or the like for administering the desired amount of solution to the patient. Rollers 16, 18 are provided, being connected together by interengaging gears 20, with rollers 16 and 18 being spaced to permit tubing 12 to pass between them in flattened manner. One or more of the rollers may carry knurls 22 or have another roughened surface so that tubing 12 will pass through the rotating rollers without slippage. As shown, rollers 16, 18 are carried in a housing 24, and tubing 12 is also stored in the same housing and positioned to pass through the roller means and be placed back into the housing.

Specifically, a removable cassette 25 defining a pair of cylindrical chambers 26, 28 is provided. Removable lid 27 of housing 24 permits installation and removal of cassette 25. Lid 27 may be removably attached with slide rods 29 as shown, or by a hinge and latch, or by any other means.

Initially, most of the tubing, which is filled with the desired liquid for administration, is coiled inside of first chamber 26, with an end portion 30 of the tubing opposed from tubing end 14 passing through rollers 16, 18 and extending through port 32 into second cylindrical chamber 28. Disc-shaped wall 34 separates the two chambers 26, 28 with the tubing in the first chamber 26 extending through central aperture 36 and then through second chamber 28 from the first chamber 26 to the rollers 16, 18.

Thus, as the rollers operate, tubing is drawn from first chamber 26 through aperture 36, with the liquid contents being expelled at the roller and being driven through the tubing and out tubing end 14, for administration in a volume which is proportional to the length of tubing passing through the rollers. The flattened tubing portion 38 from which the liquid has been expelled passes through port or first peripheral aperture 32 so that the second cylindrical chamber 28 will receive the emptied tubing from the roller means. It is preferred for the walls of particularly the second cylindrical chamber 28 to be made of a low frictional material such as polyethylene or polytetrafluoroethylene so that the tubing portion 38 which enters second chamber 28 can be directed by the cylindrical walls into a spiral configuration, so that ultimately the majority of the tubing in the system resides in the second chamber in spiral or at least coiled configuration at the termination of the solution administration process. From 12 to 30 inches of tubing, for example, can be processed in this manner. Thus as rollers 16, 18 rotate, administering the continuous, uniform ultra low dosages of liquid which are uniquely available by the invention of this application, the tubing slowly uncoils from the first chamber 26, migrating through the rollers, and then recoiling in the second chamber 28.

Tubing 12 also extends through second peripheral aperture 39 in first chamber 26, with end 14 projecting outwardly therefrom.

Roller 16 carries an extension 42 which permits one to manually turn the rollers, advancing the tubing 12 a desired distance in the event that a substantial bolus of medicament is immediately needed. The rollers may be equipped with a conventional click system so that one can determine the exact amount of rotation by counting clicks, and thus one can provide any desired quantity of liquid when desired.

Means are also provided for rotating the roller means on a spontaneous basis to advance the tubing therethrough. For example, one preferred means for rotating the roller means comprises a shaft 44 carrying roller 16. An arm 46 extends normally of the shaft and is carried thereby to rotate the shaft and roller means as the arm is moved in one direction 47. However, an overrunning clutch 48 may be provided so that when the arm is moved in a direction opposite to the one direction 47, back rotation of shaft 44 is prevented. Thus as arm 46 reciprocates back and forth rollers 16, 18 rotate. Spring 50 may be provided to bias arm 46 against cam 52 and to particularly bias arm 46 into the direction opposite from direction 47.

Overrunning clutches suitable for use herein are available from the Torrington Company of Torrington, Connecticut.

Cam 52 may be operated by motor 54 which may be a battery operated electric motor and gear box. For example a battery operated electric motor is available which can provide 2833 rpm at 2 volts. Gear box 56 may be provided having a gear ratio of 2040:1. Accordingly, cam 52 can rotate at 1.35 rpm for example.

Figure 3:
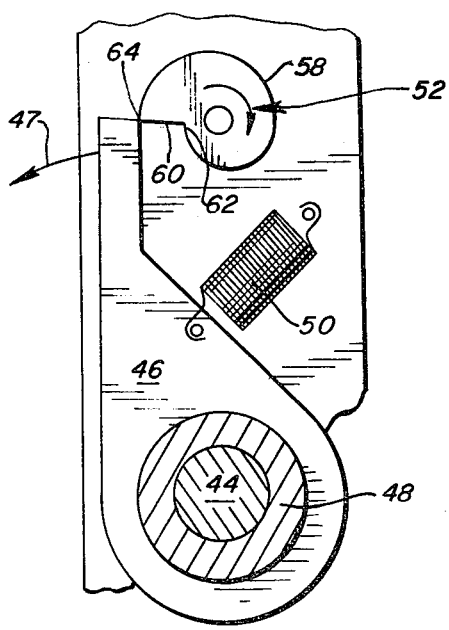
FIG. 3 is a sectional view taken along line 4—4 of FIG. 2.

As shown, cam 52 preferably has an outer bearing surface 58 which defines in transverse cross section as shown in FIG. 3 a uniformly outwardly extending spiral surface extending essentially 360° about the cam 52. A radially positioned step surface 60 extends between the beginning 62 and the end 64 of spiral surface 58.

Figure 4:
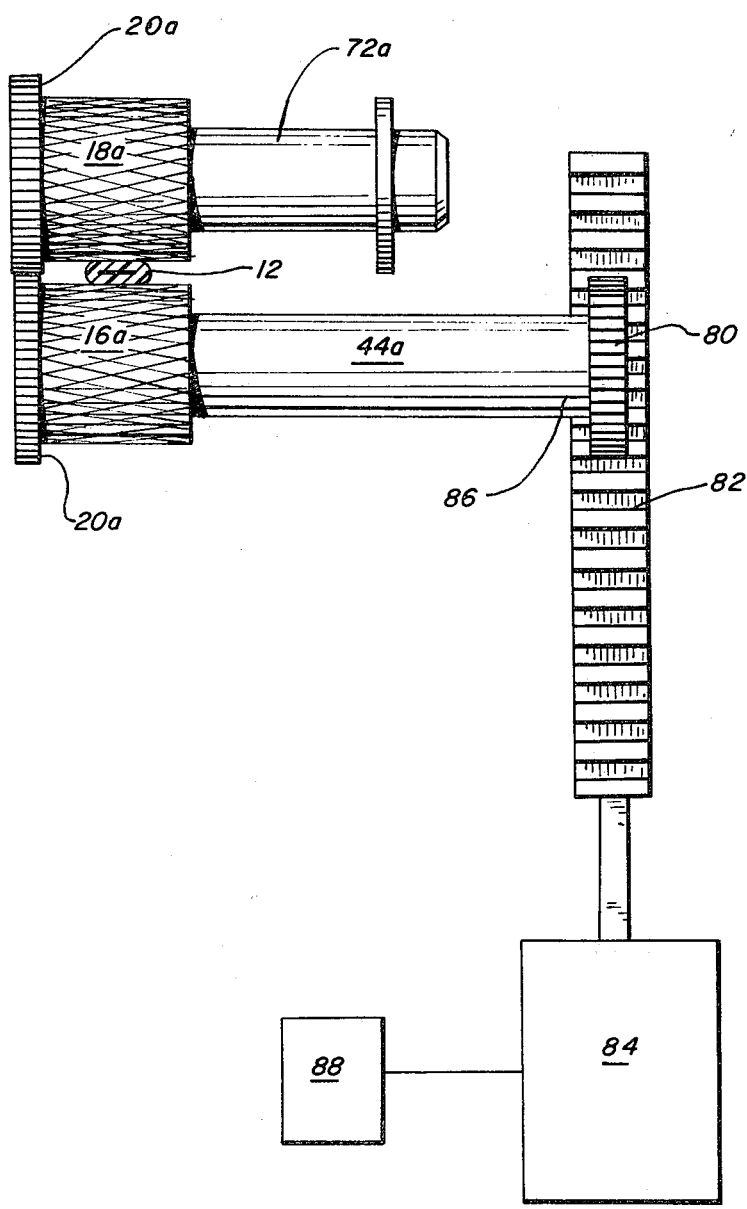
FIG. 4 is a partially diagrammatic view of an alternative design for the means for rotating the rollers.

As the result of this, as cam 52 rotates by motor 54 in counterclockwise manner as shown, arm 46 initially may be at point 62 at the beginning of the spiral surface, and is forced to rotate in direction 47 about shaft 44 as the spiral surface 58 rotates, forcing cam 46 outwardly in direction 47 until it reaches the end of spiral surface 64 as specifically shown in FIG. 4. At this point, arm 46 suddenly falls radially inwardly, impelled by spring 50, along radial step surface 60, back into contact with the beginning point 62 of spiral surface 58 again. During this period, rollers 16, 18 are rotated at a speed which is dependent upon the rotation rate of cam 52. The time taken for arm 46 to drop out of engagement with point 64 and to enter into engagement with point 62 is practically instantaneous, substantially less than a second, following which arm 46 begins to be driven outwardly again. As arm 46 falls from point 64 to point 62, the overrunning clutch 48 prevents any back rotation of shaft 44, so the only effect on rollers 16, 18 is a transient halt of rotation, typically substantially less than a second, having little effect on the accuracy of delivery.

If desired, a desmedromic cam system, without spring 50, can be used.

It can be seen that the rollers 16, 18 can be set up to rotate very slowly. The range of motion of arm 46 in terms of degrees of rotation of shaft 44 can be very low. Thus, ultra low dosages of liquid can be administered over a 24 hour period by the apparatus of this invention. The precise amount of dosage will, of course, vary with the internal volume of the lumen of tubing 12 which can be any size desired, ranging down to a lumen size of a few microns. For example, the cellulose-based hollow filaments used in hollow fiber dialyzers can be used as tubing 12 in this invention for the administration of practically microscopic amounts of liquid uniformly and continuously over a 24 hour period, or larger bore tubing as may be desired can be used. While the tubing inner diameter is usually uniform, tubing of varying inner diameter may also be used for variable fluid delivery at constant roller velocity.

As shown, shaft 44 may be conventionally secured into an apertured block 66 by a washer 68 and bolt 70. Shaft 72 carries roller 18, and may be secured in its portion of block 66 by similar means. Roller 18 may be an idler roller while, as shown, roller 16 is driven.

If desired, the end of arm 46 which bears against cam 52 may carry a roller bearing or the like, or other friction reducing means may be used as desired.

As one advantage of the system of this invention, substantially uniform rotary motion of rollers 16 and 18 are produced out of a single arm and cam system when cam 52 is shaped in the manner disclosed. If desired, the connection between arm 46 and cam 52 may be desmedromic in nature to eliminate the need for spring 50.

Auxiliary equipment in the apparatus of this invention may include a battery 74 and an electronic system 76 which provides a uniform voltage to motor 54 for uniformity of operation. An example of such an electronic system is disclosed in the patent application of Gary Feldman, Serial No. 243,539, filed Mar. 13, 1981, and entitled "Voltage Regulator". Alternatively, a tachometer circuit using Hall effect switches for counting shaft rotations may be used, while converting that data to a rotational velocity by conventional circuitry. Various speeds of operation of the motor of this invention may be provided in conventional manner by means of a variable resistor or the like.

Referring to FIG. 4, an alternate system for powering the pump of this invention is provided. As in the previous embodiment, rollers 16a, 18a rotate together by an interlocking gear system 20a to compress tubing 12 between them. Roller 18a rotates on a freewheeling shaft 72a as in the previous embodiment, while roller 16a is carried by shaft 44a, which may also be similar to the previous embodiment with the exception that it carries a gear 80, rather than the previously described transverse arm and clutch system. Gear 80 is in rotating relation with a toothed rack 82, which can be advanced in a longitudinal manner by the action of solenoid 84, to rotate gear 80 in one direction. Following this, rack 82 can be retracted, with gear 80 rotating in the opposite direction, but a conventional clutch 86 can be provided to permit the rotation of shaft 44a and roller 16a in only one direction. Thus gear 80 rotates shaft 44a when rack 82 is advanced, but shaft 44a is not rotated when gear 80 rotates in response to the retraction of rack 82.

Accordingly, every time solenoid 84 is actuated, rollers 16a, 18a are rotated a predetermined amount, to pass tubing 12 a predetermined distance through the rollers and to expel a predetermined amount of solution through the end of tubing 12.

Thus solenoid 84 may be timed by conventional means to advance rack 82 in a uniform sequence of timed advances ranging, for example, from 3 to 15 seconds between each advancement, with rack 82 withdrawing after each advancement. Accordingly, a pulse of solution is expelled through the tube 12 each time rack 82 is advanced, so that the overall amount of liquid administered over an extended period of time can be controlled, depending upon the frequency of actuation of solenoid 84 to advance rack 82. Appropriate controls 88 can be provided to properly time the solenoid's actuation.

The above has been offered for illustrative purposes only, and is not intended to limit the scope of the invention of this application, which is as defined in the claims below.

That which is claimed is:

1. Apparatus for the administration of solution at a precisely controlled rate, which comprises a length of flexible, collapsible tubing filled with said solution and connectable at one end to a conduit communicating with the vascular system of a patient, roller means for gripping and squeezing said tubing, means for rotating said roller means to advance the tubing therethrough, to expel said solution through said one end at a rate proportional to the rate of advancement of the tubing through the roller means, said means for rotating the roller means comprising a shaft carrying a roller of the roller means, an arm extending normally of said shaft and carried thereby to rotate said shaft and roller means as the arm is moved in one direction, clutch means to prevent back rotation of said shaft as the arm is moved in a direction opposite to the one direction, a motor, and cam means rotatable by said motor and positioned to engage said arm, to movingly reciprocate said arm back and forth in said one and opposite directions.

2. The apparatus of claim 1 in which spring means are provided to bias said arm against the cam means.

3. The apparatus of claim 1 in which said cam means defines an outer bearing surface for engaging the arm, said outer bearing surface defining in transverse cross section a uniformly outwardly extending spiral surface essentially 360° about the cam means, and an essentially radial step surface extending between the beginning and end of said spiral surface, whereby essentially continuous solution administration can be provided.

4. The apparatus of claim 1 in which said roller means comprises a pair of rotationally interengaged rollers between which said tubing extends.

5. The apparatus of claim 1 in which said tubing is stored in a housing and positioned to pass through said roller means and be placed back into said housing.

6. The apparatus of claim 5 in which said tubing is coiled inside of a first cylindrical chamber of a housing, said tubing being placed back into a second cylindrical chamber of said housing after passing through the roller means, said first and second cylindrical chambers being separated by a disc-shaped wall.

7. The apparatus of claim 6 in which said disc-shaped wall defines a central aperture, said tubing extending through said aperture from first chamber to the roller means, said second cylindrical chamber defining a first peripheral aperture to receive tubing from said roller means.

8. The apparatus of claim 7 in which said first chamber defines a second peripheral aperture, the one end of said tubing extending therethrough for connection with the conduit.

9. The apparatus of claim 1 in which means for manual rotation of said roller means are present.

10. Apparatus for the administration of solution to a patient at a precisely controlled rate, which comprises a length of flexible, collapsible tubing filled with said solution and connectable at one end to a conduit communicating with the vascular system of a patient, a pair of rotationally interengaged rollers for gripping and squeezing the tubing therebetween, means for rotating said rollers to advance the tubing therethrough, to expel said solution through said one end at a rate proportional to the rate of advancement of the tubing through the rollers, said means for rotating the rollers comprising a shaft carrying one of the rollers, an arm extending normally of the shaft and carried thereby to rotate said shaft and rollers as the arm is moved in one direction, transmission means to prevent back rotation of said shaft as the arm is moved in a direction opposite to the one direction, a motor, and cam means rotatable by said motor and positioned to engage said arm to movingly reciprocate said arm back and forth in said one and opposite directions, said cam means defining an outer bearing surface for engaging the arm, said outer bearing surface defining in transverse cross section a uniformly outwardly extending spiral surface essentially 360° about the cam means and an essentially radial step surface extending between the beginning and end of said spiral surface, whereby essentially continuous solution administration can be provided, and spring means provided to bias said arm against the cam means.

11. The apparatus of claim 10 in which said tubing is stored in a housing and positioned to pass through said roller means and to be placed back into said housing.

12. The apparatus of claim 11 in which said tubing is coiled inside of a first cylindrical chamber of a housing, said tubing being placed back into a second cylindrical chamber of said housing, said first and second cylindrical chambers being separated by a disc-shaped wall.

13. The apparatus of claim 12 in which said disc-shaped wall defines a central aperture, said tubing extending through said aperture from the first chamber through the second chamber to the roller means, said second chamber defining a first peripheral aperture to receive tubing from said roller means, said first chamber also defining a second peripheral aperture, the one end of said tubing extending therethrough for connection with the conduit.

14. The apparatus of claim 13 in which means for manual rotation of said roller means are also present.

15. Apparatus for the administration of solution to a patient at a precisely controlled rate, which comprises a length of flexible, collapsible tubing filled with said solution and connectable at one end to a conduit communicating with the vascular system of a patient, roller means for gripping and squeezing said tubing, means for rotating said roller means to advance the tubing therethrough, to expel said solution through said one end at a rate proportional to the rate of advancement of said tubing through the roller means, said means for rotating the roller means comprising interengaging gear and rack means, and intermittent power means for advancing and retracting said rack means to correspondingly rotate the gear means, and transmission means to prevent back rotation of said roller means as the arm is moved in one direction while permitting rotation of the roller means while the arm moves in the other direction.

16. The apparatus of claim 15 in which the means for actuating the rack is a solenoid and timer means for intermittently actuating said solenoid on a predetermined time schedule whereby said roller means intermittently move in rotation to advance the tubing therethrough at an overall predetermined rate of advancement.

17. The apparatus of claim 16 in which said roller means comprises a pair of rotationally interengaged rollers between which said tubing extends.

18. The apparatus of claim 17 in which said tubing is stored in the housing and positioned to pass through said roller means and to be placed back into said housing.

19. The apparatus of claim 18 in which said tubing is coiled inside of a first cylindrical chamber of a housing, said tubing being placed back into a second cylindrical chamber of said housing after passing through the rollers, said first and second cylindrical chambers being separated by a disc-shaped wall.

20. The apparatus of claim 18 in which said disc-shaped wall defines a central aperture, said tubing extending through said aperture from the first chamber through the second chamber to the roller means, said second chamber defining a first peripheral aperture to receive tubing from said roller means, said first chamber also defining a second peripheral aperture, the one end of said tubing extending therethrough for connection with the conduit.

21. The apparatus of claim 19 in which means for manual rotation of said roller means are present.

22. Apparatus for the administration of solution to a patient at a precisely controlled rate, which comprises a length of flexible, collapsible tubing filled with solution and connectable at one end to a conduit communicating with the vascular system of a patient, roller means for gripping and squeezing said tubing, means for rotating said roller means to advance the tubing therethrough, to expel said solution through said one end at a rate proportional to the rate of advancement of the tubing through the roller means, a cassette having a first cylindrical chamber, said tubing being coiled inside of said first cylindrical chamber of said cassette, said tubing being placed back into a second cylindrical chamber of said cassette after passing through the roller means, said first and second cylindrical chambers being separated by a disc-shaped wall.

23. The apparatus of claim 22 in which said disc-shaped wall defines a central aperture, said tubing extending through said aperture from the first chamber to the roller means, said second cylindrical chamber defining a first peripheral aperture to receive tubing from said roller means.

24. The apparatus of claim 22 in which said first chamber defines a second peripheral aperture, the one end of said tubing extending therethrough for connection with the conduit.

25. The apparatus of claim 24 in which means for manual rotation of said roller means are present.

26. The apparatus of claim 25 in which said roller means comprises a pair of rotationally interengaged rollers between which said tubing extends.

27. The apparatus of claim 1 in which said tubing is carried in a removable cassette.

28. The apparatus of claim 10 in which said tubing is carried in a removable cassette, said cassette defining a pair of cylindrical chambers with opposed ends of the tubing each coiled in a separate cylindrical chamber.

29. The apparatus of claim 28 in which said cylindrical chambers are separated by an apertured wall, said tubing extending between said chambers through the aperture of said wall.

30. The apparatus of claim 29 in which said tubing extends between each of said chambers and the exterior through a peripheral aperture.

31. The apparatus of claim 15 in which said tubing is carried in a removable cassette.

32. The apparatus of claim 22 in which the said cassette comprising a housing defining first and second cylindrical chambers separated by a disc-shaped wall, the majority of said tubing being coiled inside of a first cylindrical chamber of said cassette with one end of said tubing being coiled in the second cylindrical chamber of said cassette, and a loop of said tubing intermediate the ends projecting outwardly from said cassette for engagement with roller means for gripping and squeezing the tubing.

33. The cassette of claim 32 in which said disc-shaped wall defines a central aperture, said tubing extending through said aperture to form said loop for engagement with the roller means, said second cylindrical chamber defining a first peripheral aperture to receive tubing from said extension of said loop.

34. The apparatus of claim 33 in which said first chamber defines a second peripheral aperture, and one end of said tubing extending therethrough for connection with a conduit for delivery of the tubing contents.

* * * * *